United States Patent [19]

Paul

[11] 4,030,976

[45] June 21, 1977

[54] PROCESS FOR PREPARING A PRODUCT HAVING A BIOLOGICAL ACTIVITY

[75] Inventor: Roger Paul, Beaumont en Auge, France

[73] Assignee: Etablissement Ani, chez Me Beck, avocat, Vaduz, Liechtenstein

[22] Filed: Dec. 15, 1975

[21] Appl. No.: 640,800

[30] Foreign Application Priority Data

Jan. 8, 1975  Switzerland ........................ 129/75

[52] U.S. Cl. ................................. 195/29; 195/79; 195/96; 195/112

[51] Int. Cl.² .......................................... C12B 1/00

[58] Field of Search ................ 195/29, 79, 120, 78, 195/99, 96, 104, 109, 112; 424/103, 110

[56] References Cited

UNITED STATES PATENTS 3,669,846  6/1972  Thuillier ............................ 195/112

OTHER PUBLICATIONS

Vendel "3,5,3'triiodothyrocarboxylic acid containing ointments" cited in Chemical Abstracts 78:101992r, 1973.

*Primary Examiner*—Raymond N. Jones
*Assistant Examiner*—R. B. Penland
*Attorney, Agent, or Firm*—Stevens, Davis, Miller & Mosher

[57] ABSTRACT

A process for preparing a product having a biological activity towards an animal, human or vegetable tissue to be treated, comprising the isolation of a bacterium from the intestines of a lower animal, a mutation of said bacterium in a liquid medium, the industrial culture of said mutant bacterium (strain No. NCIB 11144 filed at the National collection of Industrial Bacteria) in a nutritious nitrogen containing medium, containing ammoniacal iron citrate and at least one phosphate, a portion of the nitrogen of said industrial culture medium being provided by an animal, human or vegetable tissue of the same source as the tissue to be treated by the product is disclosed.

7 Claims, No Drawings

PROCESS FOR PREPARING A PRODUCT HAVING A BIOLOGICAL ACTIVITY

This invention concerns a process for preparing a product having biological activity towards an animal, human or vegetable tissue to be treated, comprising the isolation of a bacterium obtained from the intestines of a lower animal, the mutation of said bacterium in a liquid medium, the industrial culture of said bacterium in a nitrogenous nutritious medium containing ammoniacal iron citrate and at least one phosphate, a portion of the nitrogen in this industrial culture medium being provided by an animal, human or vegetable tissue from the same source as the tissue to be treated with the product, characterized in that the bacterium used obtained by said mutation is No NCIB 11144 bacterial strain (filed at the National Collection of Industrial Bacteria, Aberdeen, Scotland).

The products obtained by carrying out the process according to the invention are not constituted by well-defined chemical species or a mixture; they can only be defined by their preparation process and their biological properties.

In accordance with the process according to the invention, the lower animal used is preferably the larva of an echinoderm, particularly an annelid, especially of hirudo medicinals (medicinal leech).

It has been found that the gram negative, optionally aerobic, very short polymorph form of bacterium, isolated from the flora of the digestive tract of an hirudo medicinalis, after mutation and industrial culture, allows the preparation of multiple and specific products having biological activities.

This bacterium, related to the enterobacteriaceae family, will be described and characterized here below, as well as the mutated strain resulting from the process according to the invention. Further, the process for manufacturing a product, and the biological properties thereof will be set out.

The media are seeded, either in tubes, or in Petri dishes. The incubation in the incubator is carried out at a temperature of 18°–22° C, for 2 or 3 days.

Then, after a few reseedings, the extremely short, almost coccusform, gram negative bacterium is easily isolated. Examined in the fresh state, it is very mobile. Most frequently it occurs as independant randomly oriented germs.

The identification tests of the original bacterium (as well as of the mutated strain) are indicated herebelow in a Table which permits a better realisation of the morphological and the reaction differences between the mutated strain and the original strain.

When the incubation of the bacterium (isolated pure strain) has been carried out at a temperature of about 18° C for 3 to 5 days, the mutation culture is proceeded with.

In order to obtain a mutated strain capable of giving, in an industrial culture, a high yield in active products and biological factors, a great number of examinations of the activity of the mutated strains obtained from successive experiments were made. Consequently, the mutation procedure according to this invention is to be carried out as follows:

First the mutation medium is prepared.

This medium must have a low total nitrogen content but must be relatively enriched in sulfur-containing amino acids, the latter condition being absolutely essential for obtaining, in accordance with this invention, the strains which are shown to be the most active in the industrial culture medium described herebelow.

A relative isotonicity of the medium is obtained by the addition of sodium chloride.

The following Example gives a composition of the mutation medium.

| | |
|---|---|
| Peptone | 2 g |
| Methionin | 0,5 – 1 g |
| Cystin | 0,5 – 1 g |
| NaCl | 5 g |
| Water | 1000 ml |

The peptone used may be pancreatic, trypsic or papaine peptone of meat or casein, preferably to a pepsic peptone. The pH is adjusted to 6.8 with soda.

The peptone, as a source of nitrogen in the mutation culture process according to this invention, can be replaced by any other suitable nitrogenous substance, of animal or vegetable origin; it is essential that the medium be relatively enriched in sulfur-containing amino acids.

Methionine and cystine may be partly or completely replaced (approximatively by the same weight) by other sulfur-containing amino acids: glutathion, cystein, homocystein.

The culture medium, as it has just been described, being obtained by dissolving its various components in water, which, preferably, is filtered; the pH is controlled, and if required ajusted to pH = 6.8.

Said medium is then sterilised at 120° C for about 30 minutes.

After cooling the medium, the latter is seeded with an inoculum taken from the original pure strain, cultured on a solid albuminous medium of animal origin, and after 3 to 5 days' incubation, as specified above in the technique for the isolation and the culture of the bacterium.

The mutation culture is carried out in any suitable vessels: tubes, erlenmeyers, flasks. It develops rapidly.

The mutation is obtained after 9 to 12 days' incubation at a temperature of 18° to 22° C.

The mutated strain is then maintained by weekly reseeding on agar/fresh blood, and in a culture at 18° C ($\pm$ 2° C).

These cultures may be kept freeze-dried or in the refrigerator for a shorter or longer period, or even years, which ensures the perenneality of the strains, all the more easily since a further and successive passage on the mutation medium, as above-mentioned, regenerates and rejuvenates the strains if necessary.

The industrial culture is then carried out.

Said industrial culture is carried out on the following medium, which is given as an Example and is not limited thereto.

| | |
|---|---|
| Peptone | 18 – 20 g |
| NaCl | 5 g |
| Ammoniacal iron citrate at 1% | 4 ml |
| Monopotassium phosphate at 1% | 1 ml |
| Disodium phosphate at 1% | 4 ml |
| Water | 1000 ml |

The pH is adjusted to 6.8 with soda.

This composition of the medium in mineral salts is the essential element of the formula for the industrial culture medium, because it is at the origin of biosyntheses from which the biological properties of the medium during its entire evolution derive.

The peptone used may be pancreatic, trypsic or papaine peptone from meat or casein, in preference to a pepsic peptone.

The peptone, as a source of nitrogen in the industrial culture process, may be replaced by any other suitable nitrogenous material of animal or vegetable origin; but it is essential that the mineral composition of the medium as above-specified, be respected. A portion of the peptone can be eventually replaced by the free amino acids used above for preparing the first mutation medium.

The medium whose composition has just been indicated, is complemented with an "animal tissue".

Here, the expression "animal tissue" must be taken in its broadest sense. An "animal tissue" indicates "blood tissue", thus the whole blood or a portion of its components only (blood cells, serum, plasma, fibrin) as well as any other animal tissue taken from muscles, organs, glands, bones or some well-defined portion of the animal body.

The weight of dry tissue extract from this "animal tissue" represents 10 to 50% of the weight of the peptones used in the basic formula of the above-specified industrial culture medium.

The animal tissue, for other preparations, can be eventually replaced by internal secretates of animal origin, e.g. amniotic fluid. In this case, additional peptone is added as a supplement to attain the same total nitrogen content.

The animal tissue is prepared in accordance with the normal rules for opotherapeutic preparations, i.e. the fat is removed, and it is kept at a low temperature until used.

In the case of the use of "blood tissue", the blood is used either whole (stabilised or not), or one or more portions thereof are used.

The animal tissue is ground extemporaneously. These operations are carried out while taking the maximum precautions for ensuring aseptic conditions as far as possible.

According to another embodiment, instead of using an animal tissue in the fresh state, the lyophilized and sterile animal tissue is used.

The animal tissue is added to the peptone containing treated medium, prepared as above-indicated. The pH is controlled, and if necessary adjusted to about pH = 6.8.

The industrial culture is carried out in any suitable vessels: for instance conical erlenmeyer flasks or flasks of any size, according to the volume of broth desired. For production on a large scale, the culture may be made in any appropriate known material, which can be sterilised, and wherein the various operations (seeding, sampling, pH adjustment) can be performed aseptically.

The medium is sterilised in an autoclave at 120° C for about 30 minutes.

After cooling the medium, it is seeded with a tank's bottom having a volume which is preferably 1/20 to 1/200 of the volume of the industrial medium to be inoculated. This tank's bottom having a composition similar to that of the industrial medium (but without the addition of animal tissue) results from the culture after seeding with an inoculum sampled from the maintenance cultures of the mutated strain.

The culture is carried out at a temperature of 18° to 20° for 15 days.

The broth which is formed for the industrial culture, is used for obtaining the product having a biological activity.

In order to do so, the broth is filtered aseptically on a bougie, a calibrated membrane, or by any other means.

According to another embodiment, the broth is filtered by any means known per se (paper, fabric, vacuum) and an antiseptic suitable for the use it is intended for is added thereto.

The original bacterium and the mutated bacterium have the following characteristics:

| Activity of the cultures at various temperatures | | |
|---|---|---|
| | original bacterium | mutated bacterium |
| at + 10° C | +− | + |
| at + 15° C | + | ++ |
| at + 18° C | +++ | ++++ |
| at + 25° C | + | + |
| at + 30° C | − | + |
| at + 37° C | − | +− |
| at + 42° C | − | |

| Morphological characteristics | |
|---|---|
| Original bacterium | Mutated bacterium |
| slight polymorphism of the coccus form to that of a very short bacterium; mobile, most often as independent randomly oriented germs - gram negative - optionally aerobic. | pronounced polymorphism = short bacterium, to a longer form (lengths varying from single to double = 3 to 6 μ) with some "bacillus" forms which can be 10 μ long, mobile. Gram negative - optionally aerobic. |

| Biochemical characteristics | | |
|---|---|---|
| | Original bacterium | Mutated bacterium |
| catalase | − | ± |
| oxidase | + | + |
| urea | − | − |
| glucose | without gas + | with gas + |
| lactose | − | − |
| ONPG | + | + |
| H₂S | − | ± |
| mannitol | + | + |
| mobility | + | + |
| LDC | + | + |
| indole | + | + |
| NO₂ | + | + |
| citrate simons | + | + |
| xylose | − | + |
| arabinose | − | − |
| levulose | ± | + |
| gelatine | + | +++ |
| agar fresh blood | grey brown colonies in a web - very little or no haemolysis. | lighter grey colonies; thick, creamy culture - complete haemolysis within 12 to 24 hours. |
| coagulated white of egg albumen | no action | rapid lysis with liquefaction spreading over a large zone. |
| coagulated beef serum. | slight grooves, very slight lysis. | deep grooves, rapid development, very marked lysis. |

| Evolution of the pH of the culture broths | | |
|---|---|---|
| | Mutation culture | Industrial culture |
| pH | 6.8 – 7.2 | 6.8 – 8.8 |

The following are some of the characteristics of the complexes having biological activities prepared by the process according to this invention:
reaction to ninhydrin: negative
reaction to biuret: positive
reaction to boiling H₂SO₄: deep orange.

The complexes having biological activities have been studied in vitro. Further, tests have shown that antimicrobial and antiviral activity in vivo is much increased and more effective because ground animal tissues corresponding to the tissues of the organs to be treated more specifically were added to the industrial culture medium as described above.

The tests with ninhydrin and biuret of the products obtained have shown that the proteins are only partly degraded since there is no release of amino acids. On the other hand, there is a degradation to peptides having kept sufficient specificity to act as "vectors", but which do not produce a proteic shock in the case of parenteral administration, whether intraveinously or intramuscularly.

These specific peptides thus act as "specific stimulators" and as "vectors" for the immunological factors elaborated. Their "vector" qualities can be applied to any therapeutical products they may be associated with.

Among the general biochemical properties of the products obtained, the following proteolytic property, which is one of its characteristics, is shown as follows:

1. the product having biological activity is first sterilized by means of an antiseptic having the minimum content which causes the destruction of the mutated bacteria;
2. a platinum wire (or stainless wire, e.g. a wire generally used for sampling for the purpose of seeding culture mediums) is immersed in the medium to which an antiseptic has been previously added;
3. aseptically, thus as though it were a matter of seeding, an injection is made in the nutritive gelatine of a normal culture tube;
4. the tube is kept in the incubator at $+18°$ C.

Even at this temperature, where enzymatic activities are much slowed down, a liquefaction is observed, which appears first at the surface (around the point in the surface which received the injection) and growing like a glove finger, and possibly even to complete liquefaction.

Said liquefaction by proteolytic action corresponds to a kind of "limited lysis". In fact it produces a perfectly clear, viscous liquid, quite different from liquid produced by liquefaction of bacteriolytic origin, said liquid is must more fluid and cloudy.

This characteristic of the products obtained completes the ninhydrin, biuret and sulfuric acid reactions described above for identiying said products.

Example of the preparation of a "pancreas" product
Two liters of culture medium are prepared as follows:

| | |
|---|---|
| peptones | 36 g |
| ammoniacal iron citrate at 1% | 8 ml |
| monopotassium phosphate at 1% | 2 ml |
| disodium phosphate at 1% | 8 ml |
| distilled water gsp | 2000 ml |
| ground de-fatted pig's pancreas | 40 g |
| pH adjusted to 6.8 | |

The mixture is sterilized for 30 minutes at 120° C. After cooling, the medium is seeded with about 50 ml of culture broth of the mutated bacterium (20 to 36 hours tank's bottom).

After 15 days at 18° C, the culture is stopped by the addition of a 30% formaldehyde solution, in an amount sufficient to give a formol medium at 1% maximum.

The medium is stirred for a few hours before filtering. The clear filtrate is kept preferably at a temperature of $+4$ to $+18°$ C, and in the dark.

Study of the Effect of the Pancreas Product

1. Experiments on the Rabbit a. In the first stage the test for hyperglycemia provoked in two rabbits by introducing a 20% glucose solution at the rate of 4 ml/kg into their stomachs.

| | Glucose (ml sol. at 20%) | Glycemia (g/l) | | | | |
|---|---|---|---|---|---|---|
| | | on an empty stomach | ½ h | 1h | 1h ½ | 2h |
| Rabbit No 1 1.400 kg | 5.6 ml | 0.96 | 1.99 | 0.92 | 1.10 | 0.90 |
| Rabbit No 2 1.500 kg | 6 ml | 0.74 | 1.70 | 0.80 | 0.95 | 0.70 |

(see FIG. I)

b. Four days later, both rabbits, whose response was similar, are given the same amount of glucose as previously but No. 1 is given 0.28 insulin units intravenously (0.7 ml of a 1/50 dilution of a 20 units/ml solution) and No. 2 is given 0.75 ml of the "pancreas product" diluted to 1/100 in physiological water, half an hour before the glucose absorption.

The results are the following:

| | Glycemia on an empty stomach | Injection | Glycemia after glucose ingestion | | | | |
|---|---|---|---|---|---|---|---|
| | | | ½ h | 1h | 1h ½ | 2h | 2h ½ |
| Rabbit No 1 | 1.10 | insulin 0.28 U | 2.05 | 1.40 | 0.90 | 0.45 | 0.82 |
| Rabbit No 2 | 0.85 | Pancreas complex 0.75 ml diluted to 1/100 | 0.90 | 0.80 | 0.85 | 0.80 | |

(see FIG. II)

The action of the insulin caused, after a certain delay, a sharp drop of glycemia, the "pancreas product" acted as a regulator. In fact: no appreciable drop of the glycemia level — no peak for hyperglycemia.

2. Experiment on Man

The provoked hyperglycemia test was effected on a healthy person at 48 hours interval (ingestion of 50 g of glucose), the second time the subject had absorbed:

The previous evening, two drops of the "pancreas product".

One hour before the glucose ingestion, two drops of the "pancreas product".

| | Glycemia in g/l | | | | | |
|---|---|---|---|---|---|---|
| | on an empty stomach | ½ h | 1h | 1h ½ | 2h | 3h |
| 1st hyperglycemia | 0.92 | 1.45 | 1.20 | 1.05 | 0.80 | 1.08 |
| 2nd hyperglycemia | 0.80 | 1.15 | 1.00 | 0.96 | 0.80 | 0.88 |

This experiment showed the "stimulator" action of the "pancreas product". The experiment on rabbits shows, as well as this "stimulator" effect, a "regulator" effect; this is very important, in the case of the treatment of diabetics since there is less risk of hypoglycemia drops.

The compositions of the mutation and industrial culture mediums are only given as an indication, the mutation medium being defined by its lack of nitrogen and a relative enrichment in sulfur containing amino acids, the industrial medium by its particular mineral salts composition, and in both cases, the nitrogen from the peptones can come from another source, for instance nutritious broths; as internal secretates used of animal origin, any other secretate can be used, e.g. amniotic fluid; the cultures are made either in an incubator or a water bath, or in an air-conditioned room or enclosure; the culture of the mutation and/or the industrial culture can be carried out in any known container, with or without stirring, with aeration under an inert gas or under an isolating layer of liquids; it is immaterial whether the mutated bacteria are aerobic or anaerobic; the incubation temperatures, at the different steps can vary ± 2° C from those indicated in the above description. The pH of the finished products having an activity can be adjusted in terms of the therapeutical uses they are intended for. The product can be subjected to a physical or chemical treatment to reduce or suppress anti-infectious activities while maintaining its "vector" and/or "stimulator" properties.

It was observed that the product has a particular affinity and specificity (even when administered per os and a fortiori when it is used parenterally) for the tissues, glands or organs it partly originates from because the industrial culture medium is complemented with these tissues, glands or organs of animal origin. Thus the product is "carried" (because of the "vector" effect) towards the tissues, glands, organs in question, and the effective activity of these various biological and anti-infectious factors, elaborated during the industrial culture is thus considerably increased.

Thus, the product obtained with an animal liver tissue will be suitable as a basis, for the treatment of liver diseases, and further acting per se as a stimulator of the liver.

Thus the "vector" effects can be stimulator or curator effects associated with the product.

It is remarkable to be able to specify that these products, suitably diluted, can be used per os or in the form or drinkable solutions. They can also enter into formulations of solutions to be used parenterally.

Further, in the form in which they are obtained at the end of an industrial culture, they can be used directly for preparing products to be administered per os in solid form (sugar-coated, pills, tablets, cachets).

In the same form, or diluted, they can enter into formulae for suppositories, should it be desired to remove the therapeutical product from the action of the digestive juices, without however using it parenterally.

Further, it is still possible to freeze dry the products so as to obtain basic products for complex formulas or intended to be dissolved again extemporaneously.

For their use in cosmetics, the products obtained can be introduced into creams or ointments.

The products having biological activities obtained by the process in accordance with this invention, on animal tissues are suitable for a number of therapeutical uses, in particular they can be associated with an active medicament in order to increase its activity. They are suitable for the preparation of all medicinal complexes which can be administered paremterally or per os. But often, said products can be used along, taking into account their own specificity.

For instance, to treat a pulmonary tuberculosis, a product based on lung tissue and a product based on blood can be used in the same way and simultaneously; in the case of tuberculosis of the kidney, a product based on kidney tissue and a product based on blood will be used in the same way and simultaneously.

The products obtained by the process according to this invention can also be used for cosmetics, and area wherein "vector" and "stimulator" of organs are particularly remarkable.

The process according to the invention, and as above-described, can also be used for preparing a vegetable stimulator having the following preparation characteristics. Nothing is altered in the previously described process, except that instead of adding an animal tissue to the peptonized medium, ground young plants are added thereto. A suitable antiseptic, very weakly diluted, is added to the medium obtained after the culture; it provides the vegetation with a stimulator.

I claim:

1. A process for preparing a product having a biological activity towards animal, human or vegetable tissue to be treated comprising culturing the bacterium strain NCIB 11144 in a nutritious nitrogen-containing medium further containing ammoniacal iron citrate and at least one phosphate with a portion of the nitrogen in this culture medium being provided by the tissue of said animal, human or vegetable tissue to be treated by the product.

2. A process according to claim 1, wherein said strain NCIB 11144 is obtained by mutation of an original bacterium isolated from the digestive tract of hirudo medicinalis.

3. A process according to claim 2, wherein agar/fresh blood is seeded with a sample from the digestive tract of said hirudo medicinalis, and cultured at a temperature of 18° to 22° C for 2 to 3 days, to isolate the original bacterium, said bacterium, after isolation, is cultured on a solid albuminous medium at a temperature of 18° to 22° C for 3 to 5 days.

4. A process according to claim 2, wherein the mutation of the original bacterium is provoked by cultering said original bacterium in a liquid medium comprising 2 g of peptone, 0.5 to 1 g of methionine, 0.5 to 1 g of cystine, 5 g of sodium chloride and 1000 ml of water, the pH of said liquid medium being adjusted to 6.8 by the addition of soda, at a temperature of 17° to 18° C for 9 to 12 days.

5. A process according to claim 2, wherein the strain obtained by said mutation is subjected to successive passages, every 5 to 8 days, in maintenance cultures, on agar/fresh blood, at a temperature of 17° to 18° C.

6. A process according to claim 2, wherein the mutated bacterium is cultured at a temperature of 18° to 20° C for 15 to 20 days in a previously sterilized nutritious medium to form a broth, said medium having a nitrogen content in an amount corresponding to 18–20 g/l of peptone, and containing 5 g/l of sodium chloride, 4 ml/l of ammoniacal iron citrate at 1%, 1 ml/l of monopotassium phosphate at 1% and 4 ml/l of disodium phosphate at 1% and which medium contains ground animal tissues and/or internal secretates of animal origin.

7. A process according to claim 6, wherein said broth obtained from the culture is filtered and an antiseptic added thereto.

* * * * *